US006861076B2

(12) United States Patent
Warrell, Jr. et al.

(10) Patent No.: US 6,861,076 B2
(45) Date of Patent: Mar. 1, 2005

(54) PROCESS FOR PRODUCING ARSENIC TRIOXIDE FORMULATIONS AND METHODS FOR TREATING CANCER USING ARSENIC TRIOXIDE OR MELARSOPROL

(75) Inventors: Raymond P. Warrell, Jr., Westfield, NJ (US); Pier Paolo Pandolfi, New York, NY (US); Janice L. Gabrilove, New York, NY (US)

(73) Assignee: Memorial Sloan-Kettering Cancer Center, New York, NY (US)

( * ) Notice: Subject to any disclaimer, the term of this patent is extended or adjusted under 35 U.S.C. 154(b) by 0 days.

(21) Appl. No.: 10/758,994

(22) Filed: Jan. 16, 2004

(65) Prior Publication Data

US 2004/0146570 A1 Jul. 29, 2004

Related U.S. Application Data

(63) Continuation of application No. 10/425,785, filed on Apr. 30, 2003, now Pat. No. 6,723,351, which is a continuation of application No. 09/189,965, filed on Nov. 10, 1998, now Pat. No. 6,770,304.
(60) Provisional application No. 60/064,655, filed on Nov. 10, 1997.

(51) Int. Cl.$^7$ .............................................. A61K 33/36
(52) U.S. Cl. ........................................................ 424/623
(58) Field of Search ....................................... 424/623

(56) References Cited

U.S. PATENT DOCUMENTS

| | | | |
|---|---|---|---|
| 132,275 A | 10/1872 | Gettings | |
| 232,807 A | 10/1880 | Dennett | |
| 3,700,498 A | 10/1972 | Kanazawa et al. | |
| 4,497,780 A | 2/1985 | Barin et al. | |
| 5,759,837 A | 6/1998 | Kuhajda et al. | |
| 6,720,011 B1 * | 4/2004 | Zhang | 424/623 |
| 6,723,351 B2 * | 4/2004 | Warrell et al. | 424/623 |
| 6,770,304 B2 | 8/2004 | Warrell et al. | |
| 2002/0013371 A1 * | 1/2002 | Warrell et al. | 514/623 |
| 2002/0183385 A1 | 12/2002 | Ellison et al. | |
| 2003/0099719 A1 * | 5/2003 | Warrell et al. | 424/623 |

FOREIGN PATENT DOCUMENTS

| | | |
|---|---|---|
| CN | 1061908 (A BS * | 6/1992 |
| CN | 1061908 | 6/1992 |
| CN | 1079391 | 12/1993 |
| CN | 1081104 | 1/1994 |
| CN | 1119113 | 3/1996 |
| CN | 1121807 | 5/1996 |
| CN | 1122700 | 5/1996 |
| CN | 1131037 | 9/1996 |
| CN | 1133725 | 10/1996 |
| DE | 43 17 331 | 12/1994 |
| FR | 2 539 993 | 3/1994 |
| JP | 51-88620 | 3/1976 |
| LV | 11667 | 6/1997 |
| WO | WO-94/02103 | 2/1994 |
| WO | WO-94/02108 | 2/1994 |
| WO | WO-95/01789 | 1/1995 |
| WO | WO-95/22336 | 8/1995 |

OTHER PUBLICATIONS

US 6,773,792, 5/2004, Lu (withdrawn)
Chen et al, In vitro studies on cellular and molecular mechanisms of arsenic trioxide in the treatment of leukemia, 1996, vol. 88 No. 3, pp. 1052–1061 (ABS).*
Cutler et al., Article IV, American Journal of the Medical Sciences, pp. 74–84, Jan. 1878.
Forkner et al., "Arsenic as a therapeutic agent in chronic myelogeneous leukemia", Jour. A.M.A. 97(1):3–5, 1931.
Stephens, et al., "The therapeutic effect of solution of potassium arsenite in chronic myeologenous leukemia", University of Rochester, pp. 1488–1502, 1936.
Neubauer, "Arsenical cancer: a review", Arsenic Committee of the Medical Research Council, pp. 192–251, 1947.
Shibuya, "Studies on experimental arsenious acid poisoning", Tokyo Jikeikai Ika Daigaku Zasshi, 86(4):653–675, 1971.
Pories et al., "Trace elements that act to inhibit neoplastic growth", Annals of New York Academy of Sciences, 199:265–273, Jun. 25, 1972.
Monfardini et al., "Survival in chronic myelogenous leukemia: influence of treatment and extent of disease at diagnosis", Cancer 31: 492–501, 1973.
Kerkvliet et al., "Immunotoxicology Studies of Sodium Arsenate–effects of Exposure on Tumor Growth and Cell–mediated Tumor Immunity", J. Environmental, vol. 4, pp. 65–79, 1980.
Ishinishi, et al., "Study on Chronic Toxicity of Arsenic Trioxide in Rats with Special Reference to the Liver Damages", Fukuok Acta Medicine, 71:27, 1980.
Arsenic, Environmental Health Criteria, 18, Geneva: WHO, 1981.
Cuzick et al., "Medicinal Arsenic and Internal Malignancies", Br. J. Cancer, 45:904–911, 1982.
Qi and Bi, Method for Removing $As_2O_3$ from Realgar, Chung Yao Tung Pao, 8(5):21–22, 1983.
Kasper et al., "Hepatic Angiosarcoma and Bronchioloalveolar Carcinoma Induced by Fowler's Solution", JAMA 252(24):3407–3408, 1984.
Zhang et al., "Clinical Study on the Treatment of Acute Promyelocytic Leukemia with Ai Ling #1", J. of Traditional Chinese and Western Medicine, vol. 4, No. 1, p. 19, 1984.
Pershagen et al., "On the Pulmonary Tumorigenicity of Arsenic Trisulfide and Calcium Arsenate in Hamsters", Cancer Letters, 27:99–104, 1985.

(List continued on next page.)

*Primary Examiner*—Alton Pryor
(74) *Attorney, Agent, or Firm*—Lerner, David, Littenberg, Krumholz & Mentlik, LLP

(57) ABSTRACT

The invention relates to the use of arsenic compounds to treat a variety of leukemia, lymphoma and solid tumors. Further, the arsenic compounds may be used in combination with other therapeutic agents, such as a retinoid. The invention also provides a process for producing arsenic trioxide formulations.

20 Claims, No Drawings

OTHER PUBLICATIONS

Shimotsuura et al., "Studies on the Antineoplastic Actions of $As_2O_3$", Shikwa Gakuho, 86:1237–1253, 1986.

Yamamoto et al., "Tumorigenicity of Inorganic Arsenic Compounds Following Intratracheal Instillations to the Lungs of Hamsters", Int. J. Cancer 40:220–223, 1987.

Lee et al., "Induction of Gene Amplification by Arsenic", Science, 241: 79–81, 1988.

Li et al., "Traditional Chinese and Western Medicine in the Treatment of 27 Patients with Malignant Lymphoma", Chinese J. Oncology, 10:61–62, 1988.

Sun, Hongde et al., "32 Cases of Acute Early Granulocytic Leukemia Treated with AI–Ling No. 1 in Combination with Chinese Medical Practice of Pattern Identification", Zhongguo Zhongxiyi Jiehe Zazhi, vol. 12(3), 170–171, 1992.

Peng, Zhang et al., "Treatment of Acute Promyelocyte Leukemia with Intraveneous Arsenic Trioxide", Chinese Journal of Hematology, vol. 17, Translation, Feb. 1996.

Arsen (III)–Sulfid $As_2S_2$, Gmelin's Arsenic, 8.sup.th Edition, 17:422–433, 1952.

Diarsendisulfid $As_2S_2$, Gmelin's Arsenic, 8.sup.th Edition, 17:417–422, 1952.

Goodman & Gilman's "The Pharmacological Basis of Therapeutics", Ninth Edition, McGraw–Hill, Health Professions Division, pp. 1659–1662.

"Inorganic Arsenci Compounds Other Than Arsine Health and Safety Guide", Health and Safety Guide No. 70, WHO, Geneva 1992.

"Xionghyuang, Realgar", Chinese Pharmacopia (1), Guangdong Science and Technology Publishing House, China, pp. 298–299, 1995.

Akao et al., "Arsenic Induces Apoptosis in B–cell Leukemic Cell Lines in Vitro: Activation of Caspases and Down–regulation of Bcl–2 Protein", British J of Hematology, 102, 1055–1060, 1998 ©Blackwell Science Ltd.

Andre et al., "The PML and PML/RARα Domains: From Autoimmunity to Molecular Oncology and From Retinoic Acid to Arsenic", Experimental Cell Research, 229:253–260, 1996 ©Academic Press, Inc. 1996.

Chemical Abstract, 63–Pharmaceuticals 11:317, 111:219272j and 111:219276p, 1987–1991.

Chen et al., "In Vitro Studies on Cellular and Molecular Mechanisms of Arsenic Trioxide ($As_2O_3$) in the Treatment of Acute Promyelocytic Leukemia: $As_2O_3$ induces $NB_4$ Cell Apoptosis with Down Regulation of Bcl–2 Expression and Modulation of PML–RARα/PML proteins", Blood 88(3): 1052–1061, Aug. 1996 .©American Society of Hematology 1996.

Chen et al., "Use of Arsenic Trioxide ($As_2O_3$) in the Treatment of Acute Promyelocytic Leukemia (APL):I. $As_2O_3$ Exerts Dose–Dependent Dual Effects on APL Cells", Blood 89(9):3345–3353, 1997 ©The American Society of Hematology 1997.

Chung et al., "Influence for Carcinoma Cell and Lymphatic Cell of Acetyl Arsonate", Yakhak Hoeji 40(5):599–607, 1996 (Abstract Only).

DE THE "L'oxyde d'arsenic: apres l'acide retinoique, un nouveau traitement cible dela leucemie aigue promyelocytaire" Medecine/Sciences, 13:867–71, 1997.

Dictionary of Inorganic Compounds, vol. 1, Ac–$C_{10}$, IC–0006667–IC–000671 (1992).

Flamigni et al, "Effect of Sodium Arsenite on the Induction and Turnover of Ornithine Decarboxylase Activity in Erythroleukemia Cells", Cell Biochemistry and Function 7:213–217, 1989.

Fluka, 1995/96 Catalog: 152–153.

Germolec et al., "Arsenic Induces Overexpression of Growth Factors in Human Keratinocytes", Toxicology and Applied Pharmacology, 141:301–318, 1996 ©Academic Press, Inc., 1996.

Huang et al., 1995, "The Clinical Study of QINGDAI Tablet for Treating Acute Promyelocytic Leukemia", China Magazine of Hematology, 16(1):26.

Konig et al., "Comparative Activity of Melarsoprol and Arsenic Trioxide in Chronic B–Cell Leukemia Lines", Blood 90(2):562–570, 1997 . ©The American Society of Hematology 1997.

Kwong et al., "Delicious Poison: Arsenic Trioxide for the Treatment of Leukemia", Blood 89:3487–8, 1997.

Lu et al., "Effective treatment of AML–M3(APL) and Their Remission Maintenance with Realgar: A Pilot Clinical and Laboratory Study on 38 Patients", Blood, 90 (10 Suppl. 1, part 1):416A, #1849, 1997.

Lu et al., "Study of Reaglar in the Treatment of Acute Promyelocytic Leukemia (APL)–a pilot clinical and laboratory study on 32 Patients", China–Korea Medical Conference '97, 1997.

Mervis, "Ancient Remedy Performs New Tricks", Science 273:578, 1996.

Neubauer, "Arsenic Cancer: A Review", Arsenical Cancer, Arsenic Committee of the Medical Research Council, pp. 192–251, 1947.

Reichl et al., "Effect of Arsenic on Cellular Metabolism after Single or Repeated Injection in Guinea Pigs", Arch. Toxicol, Suppl. 13, p. 363–65, 1989.

Remington's Pharmaceutical Sciences, Mack Publishing Co., Easton, PA, pp. 1570–1580, 1990.

Schenk, Handbook of Preparative Inorganic Chemistry, 1:603, G. Brauer, Ed., Academic Press, New York, 2.sup.nd Edition, 1963.

Shen et al., "Use of Arsenic Trioxide ($As_2O_3$) in the Treatment of Acute Promyelocytic Leukemia (APL):II Clinical Efficacy and Pharmacokinetics in Relapsed Patients", Blood 89(9):3354–3360, 1997 ©The American Society of Hematology 1997.

Soignet et al., "Complete Remission after Treatment of Acute Promyelocytic Leukemia with Arsenic Trioxide", J of Medicine 339:19, 1998 . ©Massachusetts Medical Society 1998.

Treleaven et al., "Arsenic and Ayurveda", Leukemia and Lymphoma, 10:343–345, 1993.

USP Dictionary of USAN and International Drug Names, United States Pharmacopeial Conventions, Inc., Rockville, MD p. 59, Nov. 1994.

Wang et al., "Studies on Chemically Preventing Leukemia", Ghung Hua Chung Liu Tsa Chih, 11(3):207–210, 1989.

Xiang et al., "60 Cases of Treating Acute Promyelocytic Leukemia by QINGDAI Tablet", Med. J. Chin. PLA 20(3):227–229, 1995.

Yuan et al., "Research on Traditional Methods for Purifying Realgar", Chung Yao Tung Pao, 13(8):23–26, 1988.

Yuan et al., "Exploring Methods for Purifying Realgar", Chung Yao Tung Pao, 13(8):17–21, 1988.

Zhang et al., "Traditional Chinese and Western Medicine in the Treatment of 27 Patients with Malignant Lymphoma," Chinese J. Oncology, 10:61–62, 1988.

Zhang et al., "Treatment of Acute Promyelocytic Leukemia with "713": Clinical Observations and Study of Action Mode on 117 patients", J. Harbin Medical Univ. 29(3):243, 1995.

Zhang et al., "Treatment of Acute Promyelocytic Leukemia with Intravenous Arsenic Trioxied", Chinese J. of Hematology 17(2) 1996.

Zhu et al., "Arsenic–induced PML Targeting Onto Nuclear Bodies: implications for the treatment of acute promyelocytic leukemia", Proc. Natl. Acad. Sci. 94:3978–3983, 1997, ©The National Academy of Sciences of the USA 1997.

"Letter on Historical Facts Regarding the Development of Ai Ling No. 1 and the Clinical Use of Arsenic Trioxide in the Treatment of Acute Promyelocytic Leukemia and a Study of It Mechanism", Heilongjiang Branch of the Chinese Medical Association, Mar. 27, 1998.

Wang et al., "Arsenic Trioxide and Melarsprol Induced Prgrammed Cell Death in Myeloid Leukemia Cell Lines and Function in PML and PNL–RARα Independent Manner", Blood, 92(5):1497–1504, 1998.

USP Dictionary of USAN and International Drug Names, United States Pharmacopeial Conventions, Inc., Rockville, MD, p. 59, Nov. 1995.

Wang et al., "Arsenic and the Treatment of Leukemia", J Harbin Medical Univ., vol. 31, No. 5, Oct. 1997.

Smorenburg et al., "Randomized Cross–Over Evaluation of Body–Surface Area–Based Dosing Versus Flat–Fixed Dosing of Paclitaxel", J. Clin. Oncology, 21:197–202 (2003).

Voisen et al., "Extrapolation of Animal Toxicity to Humans: Interspecies Comparisons in Drug Development", Regulatory Toxicology and Pharmacology, 12:107–116 (1990).

Freirich et al., "Quantitative Comparison of Toxicity of Anticancer Agents in Mouse, Rat, Hamster, Dog, Monkey and Man", Cancer Chemotherapy Reports, 50:219–244 (1966).

Gurney, "How to Calculate the Dose of Chemotherapy", Brit. J. Cancer, 86:1297–1302 (2001).

Sharkey et al., "Body Surface Area Estimation in Children Using Weight Alone: Application in Paediatric Oncology", Brit. J. Cancer, 85(1):23–8 (2001).

Au et al., "Arsenic Trioxide in Comparison with Chemotherapy and Bone Marrow Transplantation for the Treatment of Relapsed Acute Promyelocytic Leukaemia", Annals of Oncology, 14:752–757 (2003).

Zhang et al., "Pathologic, Cytogenetic and Molecular Assessment of Acute Promyelocytic Leukemia Patients Treated with Arsenic Trioxide ($As_2O_3$)", Modern Pathology; (2000); pp. 954–961.

Westervelt et al.; "Sudden Death Among Patients with Acute Promyelocytic Leukemia Treated with Arsenic Trioxide"; Blood (2001); vol. 98, No. 2, pp. 266–271.

Soignet et al.; "United States Multicenter Study of Arsenic Trioxide in Relapsed Acute Promyelocytic Leukemia", Journal of Clinical Oncology, (2001), vol. 19, No. 18, pp. 3852–3880.

Weservelt et al., "Response and Toxicity Associated with Dose Escalation of Arsenic Trioxide in the Treatment of Resistant Acute Promyelocytic Leukemia", Blood 90 (10) (1997), p. 2496.

Soignet et al., "Initial Clinical Study of a Novel Organic Arsenical, Melarsoprol, in Patients with Advanced Leukemia", Blood (W.B., Saunders, Philadelphia, PA), vol. 88, No. 10, p. 219A (ISSN:0006–4971) (1996).

* cited by examiner

PROCESS FOR PRODUCING ARSENIC TRIOXIDE FORMULATIONS AND METHODS FOR TREATING CANCER USING ARSENIC TRIOXIDE OR MELARSOPROL

1. FIELD OF INVENTION

The present invention relates to methods and compositions for the treatment of leukemia, lymphoma and certain other cancers.

More specifically, the present invention relates to the novel uses of arsenic trioxide and an organic arsenic compound for treating acute leukemia and chronic leukemia.

2. BACKGROUND OF THE INVENTION

2.1. Cancer

Cancer is characterized primarily by an increase in the number of abnormal cells derived from a given normal tissue, invasion of adjacent tissues by these abnormal cells, and lymphatic or blood-borne spread of malignant cells to regional lymph nodes and to distant sites (metastasis). Clinical data and molecular biologic studies indicate that cancer is a multistep process that begins with minor pre-neoplastic changes, which may under certain conditions progress to neoplasia.

Pre-malignant abnormal cell growth as exemplified by hyperplasia, metaplasia, and dysplasia (for review of such abnormal growth conditions, see Robbins and Angell, 1976, Basic Pathology, 2d Ed., W. B. Saunders Co., Philadelphia, pp. 68–79) precedes the formation of a neoplastic lesion. A neoplastic lesion may evolve clonally to grow into a solid tumor, and develop an increasing capacity for invasion, growth, metastasis, and heterogeneity, especially under conditions in which the neoplastic cells escape the host's immune surveillance (Roitt, I., Brostoff, J and Kale, D., 1993, Immunology, 3rd ed., Mosby, St. Louis, pps. 17.1–17.12).

Leukemia refers to malignant neoplasms of the blood-forming tissues. Transformation to malignancy typically occurs in a single cell through two or more steps with subsequent proliferation and clonal expansion. In some leukemias, specific chromosomal translocations have been identified with consistent leukemic cell morphology and special clinical features (e.g., translocations of 9 and 22 in chronic myelocytic leukemia, and of 15 and 17 in acute promyelocytic leukemia). Acute leukemias are predominantly undifferentiated cell populations and chronic leukemias more mature cell forms.

Acute leukemias are divided into lymphoblastic (ALL) and non-lymphoblastic (ANLL) types. They may be further subdivided by their morphologic and cytochemical appearance according to the French-American-British (FAB) classification or according to their type and degree of differentiation. The use of specific B- and T-cell and myeloid-antigen monoclonal antibodies are most helpful for classification. ALL is predominantly a childhood disease which is established by laboratory findings and bone marrow examination. ANLL, also known as acute myeloblastic leukemia (AML), occurs at all ages and is the more common acute leukemia among adults; it is the form usually associated with irradiation as a causative agent.

Chronic leukemias are described as being lymphocytic (CLL) or myelocytic (CML). CLL is characterized by the appearance of mature lymphocytes in blood, bone marrow, and lymphoid organs. The hallmark of CLL is sustained, absolute lymphocytosis (>5,000/$\mu$L) and an increase of lymphocytes in the bone marrow. Most CLL patients also have clonal expansion of lymphocytes with B-cell characteristics. CLL is a disease of older persons. In CML, the characteristic feature is the predominance of granulocytic cells of all stages of differentiation in blood, bone marrow, liver, spleen, and other organs. In the symptomatic patient at diagnosis the total WBC count is usually about 200,000/$\mu$L, but may reach 1,000,000/$\mu$L. CML is relatively easy to diagnose because of the presence of the Philadelphia chromosome.

The very nature of hematopoietic cancer necessitates using systemic chemotherapy as the primary treatment modality. Drugs selected according to sensitivities of specific leukemias are usually given in combination. Radiation therapy may be used as an adjunct to treat local accumulations of leukemic cells. Surgery is rarely indicated as a primary treatment modality, but may be used in managing some complications. Bone marrow transplantation from an HLA-matched sibling is sometimes indicated.

2.2. Arsenic and its Medical Uses

Arsenic has been considered to be both a poison and a drug for a long time in both Western and Chinese medical practices. In the latter part of the nineteenth century, arsenic was used frequently in attempts to treat diseases of the blood in the West. In 1878, it was reported that treatment of a leukemic patient with Fowler's solution (a solution containing potassium arsenite, valence +5) reduced markedly the count of white blood cells (Cutler and Bradford, Am. J. Ned. Sci., January 1878, 81–84). Further interests in the use of Fowler's solution as a palliative agent to treat chronic myelogenous leukemia (CML) was described by Forkner and Scott in 1931 (J. Am. Med. Assoc., 1931, iii, 97), and later confirmed by Stephens and Lawrence in 1936 (Ann. Intern. Med. 9, 1488–1502). However, while the active chemical ingredient(s) of Fowler's solution was not determined, its toxicity was well recognized. Fowler's solution was administered strictly as an oral composition, and was given to leukemic patients as a solution until the level of white blood cells was depressed to an acceptable level or until toxicities (such as skin keratoses and hyperpigmentation) developed, while the patients enjoyed varying periods of remission. In the 1960's, Fowler's solution was still used occasionally in attempts to treat CML, however, most patients with CML were treated with other chemotherapeutic agents, such as busulfan, and/or radiation therapy (Monfardini et al., Cancer, 1973, 31:492–501).

Paradoxically, one of the long recognized effects of exposure to arsenic, whether the source is environmental or medicinal, is skin cancer (Hutchinson, 1888, Trans. Path. Soc. Lond., 39:352; Neubauer, 1947, Br. J. Cancer, 1:192). There were even epidemiological data to suggest that the use of Fowler's solution over long periods could lead to an increased incidence of cancer at internal sites (Cuzick et al., Br. J. Cancer, 1982, 45:904–911; Kaspar et al., J. Am. Med. Assoc., 1984, 252:3407–3408). The carcinogenicity of arsenic has since been demonstrated by the fact that it can induce chromosomal aberration, gene amplification, sister chromatid exchanges and cellular transformation (See e.g., Lee et al., 1988, Science, 241:79–81; and Germolec et al., Toxicol. Applied Pharmacol., 1996, 141:308–318). Because of the known carcinogenic effect of arsenic, its only therapeutic use in human in Western medicine today is in the treatment of tropical diseases, such as African trypanosomiasis, (the organic arsenical, melarsoprol; See Goodman & Gilman's The Pharmacological Basis of Therapeutics, 9th edition, chapter 66, 1659–1662, 1997).

In traditional chinese medicine, arsenous acid or arsenic trioxide paste has been used to treat tooth marrow diseases, psoriasis, syphilis and rheumatosis (Chen et al., 1995, in Manual of Clinical Drugs, Shanghai, China, Shanghai Institute of Science and Technology, p.830). In 1970's, arsenic trioxide had been applied experimentally to treat acute promyelocytic leukemia (APL) in China (commented by Mervis, 1996, Science, 273:578). The clinical efficacy of arsenic trioxide has recently been re-investigated in 14 of 15 patients with refractory APL, where the use of an intravenous dose at 10 mg/day for 4–9 weeks was reported to result in complete morphologic remission without associated bone marrow suppression (Shen et al., 1997, Blood, 89:3354–3360). It was also shown that arsenic trioxide induced apoptosis (programmed cell death) in vitro in NB4 cells, an APL cell line, and that apoptosis was apparently associated with down-regulation of the oncogene bcl-2, and intracellular redistribution of the chimeric PML/RARα protein that are unique to APL cells (Chen et al., 1996, Blood, 88:1052–1061; Andre et al., 1996, Exp. Cell Res. 229:253–260). It has been reported that the biological activity of arsenic is due to the ability of arsenic to direct the nucleoplasmic fraction of PML to nuclear bodies for degradation (Zhu et al., 1997, Proc. Natl. Acad. Sci., 94:3978–3983).

Although arsenic is well known to be both a poison and a carcinogenic agent, there have been many reports concerning the use of arsenic in medical treatment. Further, from the above discussion, it should be clear that there are many different types of leukemias, each of which requires a unique treatment protocol that is modified according to the presence of factors predicting for a risk of treatment failure. Thus, the development of a broad spectrum anti-leukemia agent that can be used alone or in combination with other existing drugs is extremely desirable.

3. SUMMARY OF THE INVENTION

Despite the conflicting reports in the art concerning benefits and risks of the administration of arsenic to patients, applicants have discovered that arsenic trioxide and the organic arsenical, melarsoprol, have broad applicability in the treatment of various types of leukemias, lymphomas, and solid tumors.

The invention described herein encompasses a method of treating leukemia, lymphoma or solid tumors comprising the administration of a therapeutically effective and non-lethal amount of arsenic trioxide or melarsoprol to a human in need of such therapy. The invention, as mentioned above also encompasses the use of combination therapy to treat leukemia, especially leukemias which are refractory to other forms of treatment.

The invention also encompasses a method for the manufacture of pharmaceutical compositions comprising arsenic trioxide.

In accordance with the present invention, arsenic trioxide or melarsoprol compounds can be used alone or in combination with other known therapeutic agents (including chemotherapeutics, radioprotectants and radiotherapeutics) or techniques to either improve the quality of life of the patient, or to treat leukemia, lymphoma or solid tumor. The arsenic compounds can be used before, during or after the administration of one or more known chemotherapeutic agents, including antitumor agents. In addition, the arsenic compounds can be used before, during or after radiation treatment.

The pharmaceutical compositions of the invention are sterile solutions suitable for intravenous injection or infusion. In another embodiment the invention encompasses a composition suitable for oral delivery; comprising arsenic trioxide or melarsoprol and a pharmaceutically acceptable excipient or carrier. In another embodiment, the invention also includes compositions suitable for topical or transdermal delivery, including but not limited to iontophoretic methods. Specific therapeutic regimens, pharmaceutical compositions, and kits are also provided by the invention.

Particular compositions of the invention and their uses are described in the sections and subsections which follow.

4. DETAILED DESCRIPTION OF THE INVENTION

Methods and compositions for the treatment of leukemia, lymphoma or solid tumors are described herein. This invention provides a method of treating acute or chronic leukemia, lymphoma, or solid tumors in a human which comprises administering to a human in need of such therapy a therapeutically effective and non-lethal amount of one or more arsenic compounds, such as arsenic trioxide or melarsoprol.

The invention also includes a method of treating leukemia in a human who has become refractory to other forms of treatment which comprises administering to a human arsenic trioxide or melarsoprol in combination with another chemotherapeutic agent, e.g., all-trans retinoic acid (ATRA).

The invention also relates to a method for the manufacture of pharmaceutical compositions comprising arsenic trioxide. It is preferred that pharmaceutical compositions of the present invention exhibit reduced toxicity, improved efficacy, improved stability during storage and use, and that the composition has a physiologically acceptable pH.

4.1. The Arsenic Compounds

As used herein, "arsenic compound" refers to a pharmaceutically acceptable form of arsenic trioxide ($As_2O_3$) or melarsoprol. Melarsoprol is an organic arsenic compound which can be synthesized by complexing melarsen oxide with dimercaprol or commercially purchased (Arsobale by Rhone Poulenc Rorer, Collegeville, Pa.). Since the non-pharmaceutically formulated raw materials of the invention are well known, they can be prepared from well-known chemical techniques in the art. (See for example, Kirk-Othmer, Encyclopedia of Chemical Technology 4th ed volume 3 pps. 633–655 John Wiley & Sons).

As used herein the terms "a therapeutic agent", "therapeutic regimen", "radioprotectant", "chemotherapeutic" mean conventional drugs and drug therapies, including vaccines, for treating cancer, viral infections, and other malignancies, which are known to those skilled in the art. "Radiotherapeutic" agents are well known in the art.

In accordance with the present invention, arsenic trioxide or melarsoprol compounds can be used alone or in combination with other known therapeutic agents (including chemotherapeutics, radioprotectants and radiotherapeutics) or techniques to either improve the quality of life of the patient, or to treat leukemia, lymphoma or solid tumor. For example, the arsenic compounds can be used before, during or after the administration of one or more known antitumor agents including but not limited to mustard compounds, nitrogen mustard, chlorambucil, melphalan, cyclophosphamide, 6-mercaptopurine, 6-thioguanine, cytarabine, 5-fluorouracil, floxuridine, methotrexate, vincristine, vinblastine, taxol, etoposide, temiposide, dactinomycin, daunorubicin, doxorubicin, bleomycin, mitomycin, cisplatin, carboplatin, estramustine phosphate, hydroxyurea, BCNU, procarbazine, VM-26, interferons, and all-trans retinoic acid (ATRA), or other retinoids (See, for example, the Physician Desk References 1997). In addition, the arsenic compounds can be used before, during or after radiation treatment.

In a specific embodiment, the arsenic compound of the invention and ATRA can be administered as a mixture. In preferred aspects, the lymphoma, leukemia or solid tumor in the human treated by the combination is refractory to general methods of treatment, or is a relapsed case of leukemia.

Any suitable mode of administration may be used in accordance with the present invention including but not limited to parenteral administration such as intravenous, subcutaneous, intramuscular and intrathecal administration; oral, and intranasal administration, and inhalation. The mode of administration will vary according to the type of cancer, and the condition of the human.

The pharmaceutical compositions to be used may be in the form of sterile aqueous or organic solutions; colloidal suspensions, caplets, tablets and cachets.

4.2. Methods of Treatment

The term "a method for treating leukemia" as used herein means that the disease and the symptoms associated with the disease are alleviated, reduced, cured, or placed in a state of remission. For example, the methods of treatment of the invention can lower the white blood cell count, or reduce lymphocytosis in a human under treatment.

The term "a method for treating lymphoma" as used herein means that the disease and the symptoms associated with the disease are alleviated, reduced, cured, or placed in a state of remission.

The term "a method for treating solid tumor" as used herein means that the disease and the symptoms associated with the solid tumor are alleviated, reduced, cured, or placed in a state of remission.

In addition, the term "a method for treating leukemic infiltration" means that the infiltration of leukemic cells out of circulation and into other organs and systems and the symptoms associated with such infiltration are alleviated, reduced, cured, or placed in a state of remission.

The term "refractory" when used herein means that the leukemia is generally resistant to treatment or cure.

As used herein, "preneoplastic" cell refers to a cell which is in transition from a normal to a neoplastic form; or cells that fail to differentiate normally; and morphological evidence, increasingly supported by molecular biologic studies, indicates that preneoplasia progresses through multiple steps.

In one embodiment, the invention provides a method for treatment of leukemia in a human comprising the administration of a therapeutically effective and non-lethal amount of arsenic trioxide or melarsoprol to the human. The invention also provides a weight-based dosing regimen, not heretofore disclosed, that maximizes the safety in humans of these otherwise highly toxic compounds.

Arsenic trioxide ($As_2O_3$) inhibits growth and induce apoptosis in NB4 acute promyelocytic leukemic cell-s. Acute promyelocytic leukemia (APL) is associated with the t(15;17) translocation, which generates a PML/RARα fusion protein between PML, a growth suppressor localized on nuclear matrix-associated bodies, and RARα, a nuclear receptor for retinoic acid (RA). PML/RARα was proposed to block myeloid differentiation through inhibition of nuclear receptor response, as does a dominant negative RARα mutant. In addition, in APL cells, PML/RARα displaces PML and other nuclear body (NB) antigens onto nuclear microspeckles, likely resulting in the loss of PML and/or NB functions. It has been suggested that high concentrations of arsenic trioxide promote apoptosis, whereas low concentrations induce partial differentiation in NB4 cells as well as cells derived from APL patients. It was postulated that $As_2O_3$ works through its ability to specifically cause PML-RARα in APL cells to be relocalized to nuclear bodies for degradation (Zhu et al., 1997, Proc. Natl. Acad. Sci. USA, 94:3978–3983). However, these findings tend to limit the use of arsenic trioxide to a subset of leukemias. See Konig et al., 1997, Blood, 90:562–570.

Unexpectedly, the inventors have discovered that both $As_2O_3$ and melarsoprol are able to inhibit cell growth, and induce apoptosis in various myeloid leukemia cell lines in a PML and PML-RARα independent manner. Thus, the inventors have discovered that, contrary to the earlier findings, arsenic trioxide and melarsoprol are both effective against a broad range of leukemias regardless of the underlying molecular mechanism that causes the neoplasia. Working examples of the effect of arsenic compounds on a number of leukemic cell lines are provided in Sections 5.1 and 5.2.

Accordingly, the arsenic compounds of the present invention can be used against a variety of leukemias, including but not limited to;

Acute lymphoblastic leukemia (ALL)
Acute lymphoblastic B-cell leukemia
Acute lymphoblastic T-cell leukemia
Acute myeloblastic leukemia (AML)
Acute promyelocytic leukemia (APL)
Acute monoblastic leukemia
Acute erythroleukemic leukemia
Acute megakaryoblastic leukemia
Acute myelomonocytic leukemia
Acute undifferentiated leukemia
Chronic myelocytic leukemia (CML)
Chronic lymphocytic leukemia (CLL)

The skilled artisan will recognize that other leukemias may be treated in accordance with the present invention.

In another embodiment, the invention provides a method for treatment of lymphoma in a human comprising the administration of a therapeutically effective and non-lethal amount of arsenic trioxide or melarsoprol to the human. Lymphoma that can be treated by the methods of the invention include but are not limited to high grade lymphoma, intermediate grade lymphoma, low grade lymphoma, and the various subclassifications.

In yet another embodiment, the invention provides a method for treatment of solid tumors, including metastasises, in humans comprising the administration of a therapeutically effective and non-lethal amount of arsenic trioxide or melarsoprol to the human. Solid tumors that can be treated by the methods of the invention include but are not limited to: cancer of the digestive tract, oesophagus, liver, stomach, and colon; skin; brain; bone; breast; lung; and soft tissues, including but not limited to various sarcomas, and preferably prostate cancer.

In various embodiments, the leukemic or tumor cells are infiltrating other organs and systems in a human, for example, the central nervous system. The methods of the invention are also applicable to reduce the number of preneoplastic cells in a human in which there is an abnormal increase in the number of preneoplastic cells.

In a specific embodiment, the invention provides a method of treatment of acute promyelolytic leukemia (APL) in a human comprising the administration of a therapeutically effective and non-lethal amount of melarsoprol to the human. The inventors discovered, as described in Section 5.2, that concentrations of melarsoprol that are cytotoxic in vitro can readily be achieved in vivo.

In one specific embodiment, the invention provides a method of treatment of chronic myelogenous leukemia (CML) in a human comprising the administration of a therapeutically effective and non-lethal amount of arsenic trioxide to the human. The inventors discovered, as described in Section 5.3, that arsenic trioxide can also induce apoptosis in a CML cell line. The therapeutic benefits of the pharmaceutical compositions of the invention comprising arsenic trioxide is far superior to that of potassium arsenite, commonly formulated as Fowler's solution.

In yet another specific embodiment, the invention provides a method of treatment of acute promyelocytic leukemia (APL) in a human, in which the APL is associated with a translocation of the RARα locus on chromosome 17 to chromosome 11, comprising the administration of a therapeutically effective amount of arsenic trioxide or melarsoprol to the human. In the majority of APL cases, RARα on chromosome 17 translocates and fuses with the PML gene located on chromosome 15, i.e., t(15;17). In a few cases RARA translocates to chromosome 11 where it fuses to the PLZF gene. Patients harboring the t(15;17) are uniquely sensitive to treatment with all-trans retinoic acid (ATRA), yielding complete remission rates of 75% to 95%. APL associated with the t(11;17) (PLZF-RARa) shows a distinctly worse prognosis with poor response to chemotherapy and little or no response to treatment with ATRA, thus defining a new APL syndrome. The present invention provides that arsenic trioxide or melarsoprol can be used to treat such cases of APL. Transgenic animal models of APL associated with t(15;17) and t(11;17) for testing the therapeutic benefits and dosages of arsenic compounds of the invention are described in Section 5.4 hereinbelow.

Humans having leukemia are sometimes refractory to conventional methods of treatment by reason of having undergone anti-leukemic therapy (e.g., chemotherapy). Thus, the invention provides a method of treatment of leukemia in a human who is not responding to conventional therapy comprising the administration of a therapeutically effective and non-lethal amount of a combination of arsenic compound and another chemotherapeutic agent, such as but not limited to, all-trans retinoic acid (ATRA) or other retinoids, to the human. The arsenic compound can either be arsenic trioxide or melarsoprol or a pharmaceutically acceptable salt thereof. The invention also encompasses the treatment of retinoid-resistant patients with an arsenic compound.

In specific embodiments, the arsenic compound of the invention and the chemotherapeutic agent can be administered either as a mixture or sequentially. When administered sequentially, the arsenic compound may be administered before or after the chemotherapeutic agent, so long as the first administered agent is still providing antileukemic activity in the human when the second agent is administered. Any of the modes of administration described herein may be used to deliver the combination. In preferred aspects, the leukemia in the human treated by the combination is refractory to general methods of treatment, or is a relapsed case of leukemia.

4.3. Process for the Manufacture of Sterile Arsenic Trioxide Solution

The arsenic compounds of the invention may be formulated into sterile pharmaceutical preparations for administration to humans for treatment of leukemias, lymphomas and solid tumors. Compositions comprising a compound of the invention formulated in a compatible pharmaceutical carrier may be prepared, packaged, labelled for treatment of and used for the treatment of the indicated leukemia, lymphoma, or solid tumor.

In one aspect, the invention provides a method for the manufacture of a pharmaceutical composition comprising a therapeutic effective and non-lethal amount of arsenic trioxide ($As_2O_3$). Arsenic trioxide (raw material) is a solid inorganic compound that is commercially available in a very pure form. However, it is difficult to dissolve $As_2O_3$ in aqueous solution. Further, the inventors are unaware of any published teachings on how to formulate $As_2O_3$ as a pharmaceutical composition suitable for injection directly into a human. Arsenic is present in solution in the +5 valence state (pentavalent) or the +3 valence state (trivalent). For example, potassium arsenite ($KAsO_2$; which is present in Fowler's solution) and salts of arsenious acid contain pentavalent arsenic. It is known that one form of arsenic is more toxic than the other. (Goodman & Gilman's The Pharmacological Basis of Therapeutics, 9th edition, chapter 66, 1660, 1997). A fresh solution of arsenic trioxide containing arsenic in the trivalent state will be gradually oxidized to pentavalent state if exposed to air for a prolonged period, and as a result of the accumulation of pentavalent arsenic, the relative toxicity of a solution of $As_2O_3$ will change over time. (Id.) Furthermore, it is observed that the total amount of arsenic in solution decreases over time. This loss of material is caused by the progressive conversion of arsenic in the solution into arsine ($AsH_3$) which is a gaseous compound at room temperature. This is particularly problematic in pharmaceutical applications if the concentration of an active ingredient in the injected material cannot be controlled. It is also undesirable to allow arsine to escape from the solution into the atmosphere because arsine is also toxic.

The inventors have experimented and successfully developed a method for formulating arsenic trioxide which overcomes the above-described problems of solubility and stability. The method comprises solubilizing solid high purity $As_2O_3$ in an aqueous solution at high pH, such as pH greater than 12. For example, a 5 M solution of sodium hydroxide may be used. To aid solubilization and obtain a clear and homogenous solution, mechanical stirring and/or gentle heating may be applied. A solution of $As_2O_3$ can also be obtained by dissolving the solid compound overnight. Typically, a solution of 1 M $As_2O_3$ is obtained by this method. However, this solution is too basic to be useful as a pharmaceutical composition.

To adjust the pH of the $As_2O_3$ solution, the solution is first diluted in water, for example, to a concentration of about 1 mg/mL, pH 12. The $As_2O_3$ solution is then back-titrated with acid, such as, hydrochloric acid (1 M to 5 M HCl), with constant stirring until the pH is about 8.0 to 8.5. Highly concentrated HCl is not suitable as it causes precipitation to occur in the $As_2O_3$ solution. The partially neutralized $As_2O_3$ solution may then be sterilized for example, by filtration (e.g., through a 0.22 μm filter), and stored in sterile vials.

To make a pharmaceutical composition that can be directly injected into a subject, the composition must be sterile, standard techniques known to the skilled artisan for sterilization can be used. See, e.g., Remington's Pharmaceutical Science. The pH of the partially neutralized $As_2O_3$ solution may be further adjusted to near physiological pH by dilution (10–100 fold) with a pharmaceutical carrier, such as a 5% dextrose solution. For example, 10 mL of a partially neutralized $As_2O_3$ solution can be added to 500 mL of a 5% dextrose solution to yield a final pH of about 6.5 to 7.5. The method of the invention reduces the oxidation of arsenic in solution. Pharmaceutical compositions containing arsenic trioxide manufactured by the method of the invention show improved stability and long shelf life.

4.4. Pharmaceutical Composition and Modes of Administration

According to the invention, the arsenic compounds and their physiologically acceptable solvates may be formulated for oral or parenteral administration.

For oral administration, the pharmaceutical preparation may be in liquid form, for example, solutions, syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical compositions may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starchglycolate); or wetting agents (e.g., sodium lauryl sulphate). The tablets may be coated by methods well-known in the art.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds may be formulated for parenteral administration by injection, e.g., by bolus injection or is continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The invention also provides kits for carrying out the therapeutic regimens of the invention. Such kits comprise in one or more containers therapeutically effective amounts of the arsenic compounds in pharmaceutically acceptable form. The arsenic compound in a vial of a kit of the invention may be in the form of a pharmaceutically acceptable solution, e.g., in combination with sterile saline, dextrose solution, or buffered solution, or other pharmaceutically acceptable sterile fluid. Alternatively, the complex may be lyophilized or desiccated; in this instance, the kit optionally further comprises in a container a pharmaceutically acceptable solution (e.g., saline, dextrose solution, etc.), preferably sterile, to reconstitute the complex to form a solution for injection purposes.

In another embodiment, a kit of the invention further comprises a needle or syringe, preferably packaged in sterile form, for injecting the complex, and/or a packaged alcohol pad. Instructions are optionally included for administration of arsenic compounds by a clinician or by the patient.

The magnitude of a therapeutic dose of an arsenic compound in the acute or chronic management of leukemia will vary with the severity of the condition to be treated and the route of administration. The dose, and perhaps dose frequency, will also vary according to the age, body weight, condition and response of the individual patient. In general, the daily dose ranges of arsenic trioxide for the conditions described herein are generally from about 0.05 to about 5 mg per kg body weight administered in divided doses administered parenterally or orally or topically. A preferred total daily dose is from about 2.5 to about 40 mg of arsenic trioxide. Preferably the arsenic trioxide formulation of the invention is given daily for a maximum of 60 days, or until remission, followed by two to ten additional cycles, each lasting about 25 days in duration. For example, depending on the body weight of a patient with acute promyelocytic leukemia, a daily dose of arsenic trioxide greater than or less than 10 mg can be administered. Alternatively, following the weight-based dosing regimen, a therapeutic effect can be obtained with a daily dose of arsenic trioxide less than 10 mg.

For treatment of solid tumor, a preferred dosing regimen involves intravenous infusion of about 0.1 to about 5 mg per kg body weight per day for 5 days. This five-day treatment protocol is repeated once per month until the tumor growth tumor is inhibited or when the tumor shows signs of regression.

As for melarsoprol, the total daily dose ranges for the conditions described herein are generally from about 0.1 to about 5 mg/kg body weight administered in divided doses administered parenterally or orally or topically. A preferred total daily dose is from about 0.5 to about 4 mg melarsoprol per kg-body weight.

The effect of the therapy with arsenic trioxide or melarsoprol on development and progression of cancer can be monitored by any methods known in the art, including but not limited to determining: levels of tumor specific antigens and putative biomarkers, e.g., carcinoembryonic antigens (CEA), alpha-fetoprotein; and changes in morphology and/ or size using computed tomographic scan and/or sonogram.

Desirable blood levels may be maintained by a continuous infusion of an arsenic compound as ascertained by plasma levels. It should be noted that the attending physician would know how to and when to terminate, interrupt or adjust therapy to lower dosage due to toxicity, or bone marrow, liver or kidney dysfunctions. Conversely, the attending physician would also know how to and when to adjust treatment to higher levels if the clinical response is not adequate (precluding toxic side effects).

Again, any suitable route of administration may be employed for providing the patient with an effective dosage of an arsenic compound. For example, oral, transdermal, iontophoretic, parenteral (subcutaneous, intramuscular, intrathecal and the like) may be employed. Dosage forms include tablets, troches, cachet, dispersions, suspensions, solutions, capsules, patches, and the like. (See, Remington's Pharmaceutical Sciences.)

The pharmaceutical compositions of the present invention comprise an arsenic compound as the active ingredient, pharmaceutically acceptable salt thereof, and may also contain a pharmaceutically acceptable carrier, and optionally, other therapeutic ingredients, for example all trans retinoic acid. The term "pharmaceutically acceptable salts" refers to salts prepared from pharmaceutically acceptable non-toxic acids and bases, including inorganic and organic acids and bases.

The pharmaceutical compositions include compositions suitable for oral, mucosal routes, transdermal, iontophoretic, parenteral (including subcutaneous, intramuscular, intrathecal and intravenous), although the most suitable route in any given case will depend on the nature and severity of the condition being treated.

In the case where an intravenous injection or infusion composition is employed, a suitable dosage range for use is, e.g., from about one to about 40 mg arsenic trioxide total daily; about 0.001 to about 10 mg arsenic trioxide per kg body weight total daily, or about 0.1 to about 10 mg melarsoprol per kg body weight total daily.

In addition, the arsenic carrier could be delivered via charged and uncharged matrices used as drug delivery devices such as cellulose acetate membranes, also through targeted delivery systems such as fusogenic liposomes attached to antibodies or specific antigens.

In practical use, an arsenic compound can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including tablets, capsules, powders, intravenous injections or infusions). In preparing the compositions for oral dosage form any of the usual pharmaceutical media may be employed, e.g., water, glycols, oils, alcohols, flavoring agents, preservatives, coloring agents, and the like; in the case of oral liquid preparations, e.g., suspensions, solutions, elixirs, liposomes and aerosols; starches, sugars, microcrystalline cellulose, diluents, granulating agents, lubricants, binders, disintegrating agents, and the like in the case of oral solid preparations e.g., powders, capsules, and tablets. In preparing the compositions for parenteral dosage form, such as intravenous injection or infusion, similar pharmaceutical media may be employed, e.g., water, glycols, oils, buffers, sugar, preservatives and the like know to those skilled in the art. Examples of such parenteral compositions include, but are not limited to Dextrose 5% w/v, normal saline or other solutions. The total dose of the arsenic compound may be administered in a vial of intravenous fluid, e.g., ranging from about 2 ml to about 2000 ml. The volume of dilution fluid will vary according to the total dose administered. For example, arsenic trioxide supplied as a 10 ml aqueous solution at 1 mg/ml concentration is diluted in 10 to 500 ml of 5% dextrose solution, and used for intravenous infusion over a period of time ranging from about ten minutes to about four hours.

An exemplary course of treatment of a patient with leukemia, lymphoma, or solid cancer can involve daily administration by intravenous infusion of arsenic trioxide in an aqueous solution at a daily dose of about 0.01 to 1 mg arsenic trioxide per kg of body weight of the patient. Preferably, about 0.15 mg arsenic trioxide per kg body weight per day is used. The course of treatment may continue until bone marrow remission is observed or when side effects are becoming serious. The course of treatment may be repeated for up to ten times over approximately 10 months with a break of about 3 to 6 weeks in between courses. The post-remission course of treatment involves infusion of arsenic trioxide at a daily dose of about 0.15 mg per kg of body weight of the patient on a daily or weekdays-only basis for a cumulative total of 25 days.

5. EXAMPLES

Described below are examples of uses of the arsenic compounds of the invention in treatment of various types of leukemia. Through these and other experiments the arsenic trioxide formulation of the invention were found to be well-tolerated in humans. For example, three APL patients were given 0.10 mg of the arsenic trioxide formulation of the invention once daily (flat dose) intravenous dose.

5.1. Arsenic Trioxide and Melarsoprol Induce Apoptosis in Myeloid Leukemia Cell Lines The activity of $As_2O_3$ and melarsoprol against myeloid leukemia cell lines, including the APL cell line NB4–306 (a retinoic acid-resistant cell line derived from NB4 that no longer expresses the intact PML-RARα fusion protein), HL60, KG-1, and the myelomonocytic cell line U937 was investigated. To examine the role of PML in mediating arsenical activity, the inventors also tested these agents using murine embryonic fibroblasts (MEFs) and bone marrow (BM) progenitors in which the PML gene had been inactivated by homologous recombination. Unexpectedly, it is found that both compounds inhibited cell growth and induced apoptosis in all cell lines tested. Melarsoprol was more potent than $As_2O_3$ at equimolar concentrations ranging from $10^{-7}$ to $10^{-5}$ mol/L. $As_2O_3$ relocalized PML and PML-RARα onto nuclear bodies, which was followed by PML degradation in NB4 as well as in HL60 and U937 cell lines. Although melarsoprol was more potent in inhibiting growth and inducing apoptosis, it did not affect PML and/or PML-RARα nuclear localization. Moreover, both $As_2O_3$ and melarsoprol comparably inhibited growth and induced apoptosis of PML+/+ and PML-/-MEF, and inhibited colony-forming unit erythroid (CFU-E) and CFU granulocyte-monocyte formation in BM cultures of PML+/+ and PML-/- progenitors. A detailed description of the methods, materials, and results of these experiments is provided in Wang et al., Blood, 1998, 92:1497–1504.

Results from the experiments show that the cytotoxic effect of both arsenicals in these cell lines is not mediated by mechanisms that are dependent on PML or PML-RAR+ expression. In most lines, melarsoprol was somewhat more potent compared with $As_2O_3$ in inhibiting growth and inducing apoptosis, and the effects of both drugs were dose dependent. As previously reported, it is confirmed that $As_2O_3$ relocalized PML protein onto nuclear bodies and induced PML and PML-RARα degradation in NB4 cells while triggering spoptosis. However, similar effects were also observed in HL60 and U937 cells which do not harbor the PML-RARα fusion gene. Moreover, melarsoprol induced apoptosis in all the cell lines tested without altering PML and/or PML-RARα.

The differentiating action of $As_2O_3$ and melarsoprol, appeared negligible in vitro, and did not appear to depend on the expression and/or modulation of PML and/or PML-RARα either. In fact, the small effect observed by the inventors in long-term cultures (up to 2 weeks), was comparable in all the cell lines tested with both compounds.

It is also found that bcl-2 downregulation, which has been previously linked to the antileukemic effects of $As_2O_3$ in APL, was also not dependent on expression of PML-RARα protein, because it occurred in the NB4 subclone 306 in which the intact protein is not detectable. Finally, to test whether PML expression was essential to the antileukemic effects of arsenicals, both agents were tested in mouse embryonic fibroblasts and BM cells from animals wherein wild-type PML had been eliminated by homologous recombination. In these cells wholly lacking PML expression, both $As_2O_3$ and melarsoprol were equally effective in inhibiting growth and inducing apoptosis, and both had similar effects on normal CFU-E and CFU-GM colony formation. Moreover, no differences between wild-type and PML-/- cells were observed. Without being limited by any theory, together, these data strongly support theory that the antileukemic effects of these arsenicals occurs independently of both PML and PML-RARα expression. These results are in keeping with the medicinal history of arsenicals for diseases that are not characterized by alterations in PML protein such as, for instance, chronic myelocytic leukemia.

The results indicate that both $As_2O_3$ and melarsoprol are broadly active as antileukemic agents in both myeloid and lymphoid diseases. In conclusion, the data indicate that cytotoxic activity is not mediated by the PML protein and therefore is not limited to diseases that are associated with alterations in PML expression. Thus, the arsenic compounds of the invention have a potentially broader therapeutic role that is not confined to APL.

5.2. Clinical Study of Melarsoprol in Patients with Advanced Leukemia

Melarsoprol, an organic arsenical synthesized by complexing melarsen oxide with dimercaprol, has primarily been used for the treatment of African trypanosomiasis. The effects of melarsoprol upon induction of apoptosis in cell lines representative of chronic B-cell lymphoproliferative disorders have been investigated, and the results are described below.

Melarsoprol (supplied as Arsobal [36 mg/mL] by Rhone Poulenc Rorer, Collegeville, Pa.) was diluted in propylene glycol at a stock concentration of 10–4 mol/L and stored at room temperature. $As_2O_3$ (Sigma, St. Louis, Mo.) was dissolved in 1.65 mol/L sodium hydroxide (NaOH) at a stock solution of 10–3 mol/L. Serial dilution ($10^{-6}$ to $10^{-9}$ mol/L) were made in RPMI 1640 media. An Epstein-Barr virus (EBV)-transformed B-prolymphocytic cell line (JVM-2), an EBV-transformed B-cell chronic lymphocytic leukemia (B-CLL) cell line (I83CLL), and one non-EBV-transformed B-CLL cell line (WSU-CLL) were used as targets. Dose-response experiments with melarsoprol ($10^{-7}$ to $10^{-9}$ mol/L) were performed over 96 hours.

Unexpectedly, the inventors found that melarsoprol caused a dose- and time-dependent inhibition of survival and growth in all three cell lines. In contrast, $As_2O_3$ at similar concentrations had no effect on either viability or growth. After 24 hours, all three cell lines treated with melarsoprol ($10^{-7}$ mol/L) exhibited morphologic characteristics of apoptosis. A prominent concentration-dependent down-regulation of bcl-2 mRNA after 24 hours of exposure to melarsoprol in WSU-CLL 183CLL, and JVM-2 cells was observed. Decrease of bcl-2 protein expression was also observed in all three cell lines, whereas $As_2O_3$ had no effect on this parameter.

Given that the in vitro data above have shown unexpectedly broad antileukemic activity for melarsoprol against both myeloid and lymphoid cells, and generally at lower concentrations than $As_2O_3$, a study was initiated to evaluate the pharmacokinetics, safety, and potential efficacy of melarsoprol in human patients with relapsed or refractory leukemia.

Eligible patients were treated with a brief IV injection daily for 3 days, repeated weekly for 3 weeks, with an additional 3 wk course in responding pts. The initial dose was 1 mg/kg on Day 1, 2 mg/kg on Day 2, and 3.6 mg/kg on Day 3 and all days thereafter. Parallel in vitro studies included culture sensitivity of fresh leukemic cells to both melarsoprol and $As_2O_3$, along with serial flow cytometric studies of surface antigen expression, apoptosis, and bcl-2 expression. Three patients with AML and one with CML have entered the study.

Using a method based on high performance liquid chromatography that is sensitive to approximately 10 mg/ml, preliminary pharmacokinetic data show that peak plasma drug concentrations were obtained immediately after injection with a Cmax that ranged from 1.2 ng/ml on day 1 to 2.4 ng/ml on day 3. While the initial distribution phase was rapid, a prolonged Thy has suggested release from a deep compartment. Plasma areas under the concentration×time curves (AUCs) were proportional to the administered dose, ranging from 0.48 ng·hr/ml on Day 1 to 1.48 ng·hr/ml on Day 3. Detectable concentrations of the drug were found in plasma one week after initial dosing. The drug has been relatively well-tolerated. Adverse effects have included transient pain at the injection site and mild nausea. No signs of "reactive encephalopathy" (occasionally observed during treatment of CNS trypanosomiasis) have been observed.

Results from these studies suggest that melarsoprol may have broader activity than inorganic $As_2O_3$, and that concentrations which are cytotoxic to leukemic cells in vitro, and thus therapeutic, are readily achieved in vivo.

5.3. Arsenic Trioxide Induces Apoptosis in K562 Chronic Myelogenous Leukemia (CML) Cells A Philadelphia chromosome positive CML cell line K562 is used to determine if arsenic trioxide ($As_2O_3$) promotes apoptosis in CML. Suspension cultures of cells in log phase were exposed to $As_2O_3$ at concentrations of $1 \times 10^{-5}$ M, $5 \times 10^{-6}$ M, and $1 \times 10^{-6}$ M. Aliquots of cells were analyzed at various time points over the course of 72 hours to assess viability and apoptosis. Viability was measured using trypan blue exclusion; at the same time, apoptosis was detected by morphology, flow cytometry, and DNA gel electrophoresis.

Arsenic trioxide at a concentration of $1 \times 10^{-6}$ M had no effect on K562 cell growth or viability. The greatest effect on cell growth and survival was seen with $1 \times 10^{-5}$ M $As_2O_3$ K562 cell growth and viability data after 72 hours of exposure to $As_2O_3$ are recorded in Table 1:

TABLE 1

|  | % Cell Growth Impairment | % Viability | p value |
|---|---|---|---|
| control | 0 | 92.1 ± 0.9 |  |
| $5 \times 10^{-6}$ M $As_2O_3$ | 63.0 | 78.8 ± 0.5 | 0.0001 |
| $1 \times 10^{-5}$ M $As_2O_3$ | 75.3 | 61.9 ± 2.9 | 0.0223 |

Evidence that this arsenic-induced decrease in viability represented apoptosis was analyzed. Morphologic features of apoptosis including membrane blebbing and nuclear condensation were evident in stained cytospins of K562 cells incubated with $10^{-5}$ M $As_2O_3$ for 72 hours. This correlated with evidence of DNA internucleosomal damage as visualized by gel electrophoresis of DNA extracted from K562 cells exposed to $10^{-5}$ M $As_2O_3$. Quantitative assessment of apoptosis, as measured by the TUNEL method demonstrated that 75.6%±8.6 ($1\times10^{-5}$ M $As_2O_3$) cells exhibited apoptosis as compared with 6.3%±3.0 (control) cells at 72 hours. Treatment of K562 cells with $10^{-5}$ M $As_2O_3$ resulted in an upregulation of p21 mRNA, as detected by Northern analysis, suggesting an arrest of the cells in the G1 phase of the cell cycle. This data indicates arsenic trioxide as a therapeutic agent for CML.

5.4. Therapeutic Trials with Retinoic Acid and Arsenic Trioxide ($As_2O_3$) in PML-RARα and PLZF-RARα Transgenic Mice Acute promyelocytic leukemia (APL) is associated with chromosomal translocations which invariably involve the translocation of the Retinoic Acid Receptor α (RARα) locus on chromosome 17 to other loci in the genome, such as in the majority of APL cases, the PML gene located on chromosome 15, and in a few cases the PLZF gene on chromosome 11. Patients harboring the t(15;17) are sensitive to treatment with All-Trans Retinoic Acid (ATRA), yielding complete remission rates of 75% to 95%. APL associated with the t(11;17) (PLZF-RARα) shows a poor response to ATRA.

To test the efficacy of $As_2O_3$ in the treatment of APL, models of the disease were created in transgenic mice. Transgenic mice were generated by standard techniques in which the expression of the PML-RARα or PLZF-RARα fusion proteins is placed under the control of a myeloid-promyelocytic specific human Cathepsin-G (hCG) mini-gene. Both hCG-PML/RARα and hCG-PLZF-RARα transgenic mice develop myeloid leukemia with features of APL similar to those in humans.

Therapeutic trials on these leukemic mice with the following regimens were started: 1) ATRA: 1.5 μg per gram of body weight per day administered orally; and 2) ATRA: 6 μg per gram of body weight per day administered intraperitoneally. Mice were bled once a week to evaluate the response.

PML/RARα leukemias responded well to ATRA with high remission rates (80% with regimen 1). Surprisingly, in vitro, ATRA induced differentiation, and inhibited growth of leukemic cells as well as leukemic colony formation in bone marrow and spleen progenitors assays in both PML-RARα and PLZF-RARα leukemias. Furthermore, in ex vivo experiments, leukemic cells from PLZF-RARα mice lost their tumorigenic capacity when transplanted in recipient nude mice upon pre-incubation with ATRA, while untreated cells were tumorigenic. However, in vivo, PLZF-RARα leukemias responded poorly to ATRA (28% with regimen 1), while higher doses of ATRA appeared more effective (50% with regimen 2). In conclusion, leukemias in PLZF-RARα transgenic mice are sensitive to ATRA treatment, but might require therapeutic regimens with high doses of ATRA. These findings have direct implications in the treatment of APL patients with t(11;17).

In both PML-RARα and PLZF-RARα leukemias, ATRA prolonged survival, but leukemias relapsed shortly after remission was achieved, and were refractory to further ATRA treatment. The two transgenic mouse models is also used to test the efficacy and dosage of $As_2O_3$, and ATRA+ $As_2O_3$ in combination for treatment of APL patients resistant to ATRA, and in APL associated with the t(11;17). A regimen of $As_2O_3$ at 6 μg per day or a combination of $As_2O_3$ at 6 μg and ATRA at 1.5 or 6 μg per gram of body weight per day is administered intraperitoneally. Mice are bled weekly to evaluate the remission of the APL.

5.5. Manufacture and Stability of Pharmaceutical Formulation

Solid ultrapure arsenic trioxide ($As_2O_3$) was solubilized in a solution of 5 M sodium hydroxide (NaOH). The suspension was stirred at ambient temperature for 5 minutes which yielded a clear, homogenous solution. The $As_2O_3$ solution (2 mL, 1.0 M) was added to 393.6 mL of $H_2O$ in a 500 ml Erlenmeyer flask, which yielded an $As_2O_3$ concentration of 1 mg/mL at pH=12. A 5.0 M HCl solution was prepared by dilution of HCl (49.26 mL, 37% wt/wt, 10/15 M) with $H_2O$ (50.74 mL) in a 250 mL Erlenmeyer flask. The HCl solution was later transferred via syringe to a 1000 mL empty evacuated container. The $As_2O_3$ solution was back titrated with HCl (0.725 mL, 5.0 M) to pH 8.0. Approximately 10 mL of the backtitrated $As_2O_3$ solution was filtered through a Millex-GS 0.22 μm filter unit and was added to each of approximately 30 sterile evacuated sterile vials. To make the pharmaceutical composition which would be injected intravenously into patients, 10 mL of this solution was withdrawn from two of the vials and was added to a 500 mL 5%-dextrose solution which yielded a final pH of 6.5.

The high purity of the bulk starting material was confirmed (see Table 1) by atomic absorptiometry. Duplicate samples of four intermediate or final-step solutions were assayed for total arsenic content. Assay bulk powder confirmed the extremely high purity of the starting material. Data for arsenic content of the intermediate and finished product solutions are presented in Table 2 below.

The data below show that the solutions are stable in that there does not appear to be any indication of weight loss of arsenic over time.

TABLE 2

Arsenic content (ppm) of intermediate formulation and finished product solution of arsenic trioxide.

| | Sample Code | | | | |
|---|---|---|---|---|---|
| | A-01* | A-02 | A-03 | A-04 | A-05 |
| Aliquot A | 140,600 | 600 | 707 | 629 | 680 |
| Aliquot B | 139,000 | 564 | 703 | 688 | 687 |
| Assay Variance | 1.1% | 6% | 0.57% | 8.7% | |

*Identity of sample codes:
A-01: Intermediate product solution after initial solubilization in NaOH.
A-02: Intermediate product solution prior to HCl titration.
A-03: Intermediate product prior to Millex filtration.
A-04: Finished product from sterile 10 ml fill vial immediately after manufacturing.
A-05: Finished product from capped vials two months after manufacturing.

6. EXAMPLES

Clinical Trials in Apl Patients

Arsenic trioxide was evaluated in patients with APL to determine whether this agent induced either cytodifferentiation or apoptosis. Twelve patients who had relapsed from extensive prior therapy were treated with arsenic trioxide at doses ranging from 0.06 to 0.2 mg/kg per day until a bone marrow remission was achieved. Bone marrow mononuclear cells were serially monitored by flow cytometry for immunophenotype, fluorescence in situ hybridization (FISH), reverse transcription polymerase chain reaction (RT-PCR) assay for PML/RAR-α expression, and Western blot expression of the apoptosis-associated proteins, caspases 1, 2 and 3. The results showed that low-doses of arsenic trioxide are highly effective for inducing complete remission in relapsed patients with APL. Clinical response is associated with incomplete cytodifferentiation and induction of apoptosis with caspase activation in leukemic cells.

6.1. Methods

Clinical protocol: Eligibility requirements included a diagnosis of APL confirmed by cytogenetics or fluorescence in situ hybridization (FISH) analysis for a t(15;17) translocation, or by reverse transcriptase polymerase reaction (RT-PCR) assay for PML/RAR-α. Patients must have relapsed from standard therapy that had included all-trans retinoic acid plus a combination of cytotoxic drugs. Signed informed consent was required, and the protocol was reviewed and approved by this center's institutional review board Arsenic trioxide treatment: Arsenic trioxide was supplied as an aqueous solution in 10 ml vials containing 1 mg/ml of drug. The drug was further diluted in 500 ml of 5% dextrose solution and infused intravenously over 2 to 4 hours once per day. While the initial cohort of patients received either 10 or 15 mg/day as a flat dose, the referral of two children prompted the invention of a weight-based regimen (0.15 mg/kg/day) that was heretofore unknown. The drug was given daily until bone marrow remission was observed. Patients who achieved complete remission were eligible for treatment with additional courses of therapy 3 to 6 weeks after the preceding course. Subsequent courses were generally given at a dose of 0.15 mg/kg/day for a cumulative total of 25 days, administered either daily or on a weekdays-only schedule, for a maximum total of 6 courses over approximately 10 months.

Monitoring during study: Patients with coagulopathy were transfused with platelets and fresh-frozen plasma to maintain the platelet count and fibrinogen at target levels $\geq$50,000 cells/cu mm and $\geq$100 mg/dL, respectively. Blood counts, coagulation studies, serum chemistry profiles, urinalyses, and electrocardiograms were serially obtained. A bone marrow aspiration and/or biopsy was performed at baseline and periodically thereafter until remission was documented.

Conventional response criteria were observed, which included recovery of bone marrow to $\leq$5% blasts, peripheral blood leukocytes $\geq$3,000 cells/cu mm, and platelets $\geq$100,000 cells/cu mm.

Cellular immunophenotype studies: Heparinized bone marrow or blood samples were collected and mononuclear cells were isolated by Ficoll-Hypaque centrifugation. Surface membrane antigens were detected by direct immunofluorescence staining using fluorescein isethiocynate (FITC) or phycoerythrin conjugated monoclonal antibodies: CD16 (Leu 11a), CD11b, CD33 (Leu M9), HLA-DR, CD45, and CD14, purchased from either Becton-Dickinson (Mountainview, Calif.) or Immunotech Immunology (Marseille, France). Dual-color staining was performed by incubating cells simultaneously with two monoclonal antibodies, including CD33-PE/CD11b-FITC and CD33-PE/CD16-FITC. Negative controls using irrelevant monoclonal immunoglobulins of the same isotype were analyzed concurrently. Flow cytometric analyses were performed on an EPICS Profile II flow cytometer (Coulter Electronics) equipped with a 488 nm argon laser. Forward and side-scatter cell parameters were measured and combined with CD45/CD14 staining to identify populations of interest and to exclude monocytes from the analysis gate. The Multiparameter Data Acquisition and Display System (MDADS, Coulter Electronics) was used to acquire and analyze data.

Fluorescence in situ hybridization (FISH): Selected specimens that had undergone immunofluorescence staining for CD33 and CD11b were sorted for cells that coexpressed both antigens using a FACStar Plus cell-sorter (Becton-Dickinson). Separated cells were incubated in culture media at 37° C. for one hour, treated with hypotonic solution 0.075M KCl for 5 minutes, fixed in 3:1 methanol:acetic acid fixative, and air-dried. Interphase FISH was performed using a specific PML/RAR-α translocation dual-color probe (Vysis; Downer's Grove, Ill.). Briefly, DNA from interphase cells was denatured by immersing slides in a solution of 50% formamide/2×SSC at 73° C. for 5 minutes; the slides were then dehydrated in alcohol and air dried. A mixture of probe in hybridization mixture was applied, covered with a cover slip, and sealed with rubber cement. Hybridization was carried out at 37° C. in a moist chamber for approximately 12 to 16 hours. Following hybridization, unbound probe was removed by washing the slides at 45° C. in 50% formamide/2×SSC solution three times for 10 minutes each, followed by a wash in 2×SSC/0.1 NP-40 solution at 45° C. for 5 minutes. Slides were then air dried and counter-stained with 4',6-diamidino-2-phenylindole and covered with a glass coverslip. Analysis of interphase cells for fluorescent signals was performed with a Photometrics Sensys camera fitted to a Zeiss axioscope. A minimum of 300 cells was studied for each sample.

Western blot analysis: Cells were lysed in a buffer containing 50 mM Tris-HCl, 0.5 mM ethylene glycol [bis][aminioacyl]tetra acetic acid, 170 mM NaCl, 1 mM dithiothreitol, 0.2% NP-40, 0.01 U/mL aprotinin, 10 μg/mL leupeptin, 10 μg/mL pepstatin, and 1 AM phenylmethylsulfonyl fluoride (all from Sigma). The lysates were then sonicated using a ultrasonic homogenizer (4710 series, Cole Parmer Instruments, Chicago, Ill.) and centrifuged at 7,500 g (Sorvall Instruments, Newtown, Conn.). Protein content of the lysates was determined using a BioRad Protein Assay Kit (Bio-Rad Laboratories, Hercules, Calif.) at 595 nm with a BSA standard. A sample buffer containing 10% glycerol, 0.4%. SDS, 0.3% bromphenol blue, 0.2% pyronin Y, in 1× stacking buffer (Tris base 0.5 M, 0.8% SDS), 20% 2-mercaptoethanol, was added to the cell lysates, which were heat-denatured at 95° C. for 3 min. Subsequently, 15 μg/lane of protein was loaded on a SDS-polyacrylamide gel containing 12.5% polyacrylamide and was size-fractionated by electrophoresis. Proteins were electroblotted onto Tras-Blot® transfer medium (Bio-Rad) and stained with Ponceau-S as an internal loading control. Rabbit anti-human monoclonal antibodies, including caspase 1, caspase 2 (both from Santa Cruz Biotechnology, Santa Cruz, Calif.), and caspase 3 (PharMingen, San Diego, Calif.) were added, and bound antibodies were detected using the ECL™ chemiluminescence detection system (Amersham, Arlington Heights, Ill.). Protein bands were quantified by computer densitometry.

RT-PCR analysis for PML/RAR-α: RT-PCR was performed using methods previously described (Miller et al., 1992, Proc. Natl. Acad. Sci. 89:2694–8; Miller et al., 1993, Blood, 82:1689–94).

6.2. Results

Patients: Twelve patients with relapsed or refractory APL were treated. All patients had received extensive prior therapy with retinoids and cytotoxic drugs (Table 3). Two patients had relapsed from allogeneic bone marrow transplantation, one of whom had also failed donor T-cell reinfusion. One patient was being maintained on hemodialysis for chronic renal failure.

Clinical Efficacy: Eleven of the 12 patients achieved a complete remission after arsenic trioxide treatment. The patient who entered on hemodialysis sustained an intracranial hemorrhage on day 1 and died on day 5. The median duration of therapy in responding patients was 33 days (range, 12 to 39 days), the median daily dose was 0.16 mg/kg (range, 0.06 to 0.2 mg/kg), and the median cumulative dose during induction was 360 mg (range, 160 to 515 mg) (Table 3). Complete remission by all criteria was attained at a median time of 47 days (range, 24 to 83 days) after initiation of therapy. Remission by bone marrow criteri—the determining factor for discontinuing therapy—was achieved first, usually followed in sequence by recovery of peripheral blood leukocytes and platelets. Over the range of doses used in this study, no differences in efficacy or time to response were obvious. After 2 courses of therapy, 8 of 11 patients tested had converted their RT-PCR assays for PML/RAR-α from positive to negative.

All 11 patients in complete remission completed at least 1 post-remission treatment course with arsenic trioxide. Four, two, and one patient each have completed a total of three, four and five treatment courses, respectively. The median duration of remission is 5+months (range, 1 to 9+months). However, 3 of the 11 patients relapsed during the second treatment course; none of these patients had converted their RT-PCR assays, and each appeared to have rapidly acquired drug resistance. Two of these individuals have since expired from progressive leukemia.

Adverse Events: The clinical condition of patients in this study was highly variable, which reflected their extensive prior therapy. The protocol did not require hospitalization; three patients completed induction therapy entirely as outpatients, and one other individual was hospitalized solely for placement of a venous catheter. However, 8 patients were hospitalized for complications of leukemia, 5 of whom required transfer to an intensive care unit, endotracheal intubation, and assisted ventilation for complications that included pulmonary hemorrhage, renal failure, sepsis, graft vs. host disease, non-specific pulmonary infiltrates, or hypotension. One patient required insertion of a permanent pacemaker after second-degree heart block developed in the setting of severe metabolic acidosis, hyperkalemia, hypotension, and renal insufficiency. However, the heart block reversed despite rechallenge with further arsenic trioxide therapy. The drug was temporarily withheld due to serious intercurrent medical complications in 5 patients for a median of 2 days (range, 1 to 5 days). Two patients developed symptoms similar to that of the "retinoic acid syndrome"; both were presumptively treated with dexamethasone and improved. Only 2 patients required no platelet transfusions whatsoever; the median number of platelet units transfused was 61 (range, 0 to 586 units).

The median total peripheral blood leukocyte count at entry was 4,700 cells/cu mm (range, 500 to 144,000 cells/cu mm). Six patients developed leukocytosis (i.e., ≧20,000 cells/cu mm) that ranged from 20,800 to 144,200 cells/cu mm. No additional therapy was administered to these patients, and the leukocytosis resolved in all cases without further intervention.

Common adverse reactions included lightheadedness during the infusion, fatigue, musculoskeletal pain, and mild hyperglycemia. Three patients developed dysesthias presumably due to peripheral neuropathy. However, 2 of these patients had been immobilized for prolonged periods during assisted ventilation, and the other patient had an antecedent neuropathic history.

Immunophenotype studies: APL is characterized by cells that express CD33, an antigen typically associated with primitive myeloid cells. Arsenic trioxide therapy induced a progressive decrease in the proportion of cells that solely expressed CD33, along with an increase in the proportion of cells that expressed CD11b, an antigen associated with mature myeloid elements. While these changes would be anticipated from any agent that induced remission in APL, arsenic trioxide also induced expression of cells that simultaneously expressed both antigens. In most cases, these dual-expressing cells dominated the myeloid cell population, and they persisted for extended periods after complete remission was achieved by clinical criteria.

Fluorescence in situ hybridization analysis: Bone marrow mononuclear cells taken from a patient both early and later in complete remission were sorted by flow cytometry for coexpression of CD33 and CD11b. Using fluorescence in situ hybridization (FISH) analysis, three hundred cells were examined early in remission. Similar to control APL cells, the majority of these cells yielded a hybrid signal, indicating a translocation between PML and RAR-α genes and their origin from the neoplastic clone. However, when cells from the same patient were again sorted using these same parameters later in remission, only the normal pattern of fluorescence signals was detected, indicating their derivation from normal hematopoietic progenitors.

Western blot analysis: Protein extracts from bone marrow mononuclear cells were serially examined by Western blot analysis. The analysis showed that the precursor forms of caspase 2 and caspase 3 were upregulated in vivo in response to arsenic trioxide treatment. Moreover, this treatment also induced expression of cleaved fragments of caspase 1, indicating activation of the enzyme. There is also some indication that expression of the cleaved form of caspase 3 is increased. The antibody used in these experiments does not react with the cleaved form of caspase 2.

6.3. Discussion

In this study, with few exceptions, patients admitted to the trial had sustained multiple relapses and were resistant to conventional chemotherapy, retinoids, or bone marrow transplantation. At entry, patients in this study suffered from numerous leukemia-related complications, including respiratory failure, disseminated Varicella zoster infection, cavitary aspergillosis, chronic renal failure, and graft-vs.-host disease. Moreover, 5 of the 12 patients required admission to an intensive care unit for assisted ventilation and supportive care, but these complications were not directly related to arsenic trioxide therapy.

Virtually all patients with a confirmed diagnosis of APL attained remission without the early mortality associated with retinoid therapy. Although less commonly observed compared with all-trans retinoic acid treatment, arsenic trioxide induced striking leukocytosis in several patients. Upon withholding other cytotoxic drugs, the leukocytosis disappeared as patients attained remission. Despite 3 early relapses, 8 of 11 patients tested converted RT-PCR assays for PML/RAR-α (a molecular marker of residual disease) to negative, a phenomenon that is unusual after all-trans retinoic acid treatment alone. Finally, arsenic trioxide is active in APL over at least a three-fold dose range from 0.06 to 0.20 mg/kg.

All-trans retinoic acid induces "terminal" differentiation of APL cells, but the cytodifferentiating effects of arsenic trioxide appear to be incomplete. Arsenic induces a population of cells that simultaneously express surface antigens characteristic of both mature and immature cells (i.e. CD11b and CD33, respectively). Early during induction, these cells retain the t(15;17) translocation that characterizes APL.

Unexpectedly, these cells persisted in the bone marrow despite the achievement of a clinically complete remission; however, later in remission, the coexpressing cells—while still readily detectable—were no longer positive by in situ hybridization. The morphologic appearance of leukemic cells during therapy is also far less distinctive than that observed during therapy with all-trans retinoic acid. In fact, leukemic cells from many patients displayed few morphologic changes for 10 or more days, after which the proportion of leukemic cells progressively decreased.

Following "non-terminal" differentiation, arsenic trioxide appeared to induce apoptosis, coincident with increased expression and conversion of cysteine proteases (termed caspases) from inactive precursors to activated enzymes. The caspase pathway has only recently been characterized as an important pathway of programmed cell death. Initially recognized due to homology between the C. elegans protein ced-3 and mammalian interleukin-1β converting enzyme (ICE), the family of caspases now encompasses at least 10 different proteins that cleave a number of polypeptides. In leukemic cell lines, caspase activation is inducible with a number of cytotoxic agents, including all-trans retinoic acid. Since these enzymes induce widespread proteolysis, it is conceivable that PML/RAR-α is a caspase substrate.

A final similarity shared by arsenic trioxide and all-trans retinoic acid is the rapid development of clinical resistance in some individuals. Leukemic cells taken from two patients who relapsed retained in vitro sensitivity over concentrations ranging from $10-4$ M to $10^{-7}$ M. Relative arsenic resistance due to decreased intracellular transport has been described in association with down-regulation of membrane transporters encoded by the ars operon in bacterial cells.

Resistance in mammalian cells is less well-characterized, but alterations in membrane transport or efflux are probably important factors.

In summary, arsenic trioxide induces complete remission in patients with APL who have relapsed from extensive prior therapy. This drug causes partial but incomplete cytodifferentiation of leukemic cells, followed by caspase activation and induction of apoptosis.

Denotes patient who died early. Other treatment: [a] mitoxantrone/etoposide; [b] allogeneic bone marrow transplantation; [c] methotrexate/vincristine/6-mercaptopurine; [d] 9-cis retinoic acid plus M195 (anti-CD33 monoclonal antibody).

7. EXAMPLES

Clinical Use in Lymphoma

Based upon the initial discovery of the antitumor effects of arsenic trioxide in vitro against B-cell lymphocyte lines, the inventors treated one patient with intermediate-grade large cell lymphoma who had relapsed from multiple forms of conventional therapy, including autologous bone marrow transplantation. Despite rapid progression of his disease prior to starting the arsenic trioxide therapy, treatment with arsenic trioxide effected a major (>50%) shrinkage in the size of his cancerous lymph nodes and spleen, which was also associated with a major improvement of his quality of life.

8. EXAMPLES

Clinical Use in Non-Hematopoietic Cancer

Arsenic trioxide was also used to treat colon cancer. In a preliminary test, one patient with colon cancer who received one treatment with arsenic trioxide showed a major reduction in his serum CEA (carcinoembryonic antigen) level. The patient received daily intravenous infusion of 0.1–5 mg arsenic trioxide per kg body weigh per day for five days. A change in the level of CEA from 19,901 ng/ml to 15,266 ng/ml, a 23% reduction, was observed. It is well known that the a reduced level of serum CEA is associated with antitumor response.

Clinical data confirms that arsenic trixoide can also be used to treat other non-hematopoietic cancer, such as colon cancer.

9. EXAMPLES

Pharmacokinetics Studies

Several dose-ranging studies were conducted to examine the pharmacokinetics (PK) and biological effects of $As_2O_3$

TABLE 3

Clinical characteristics and induction therapy results of patients with acute promyelocytic leukemia treated with arsenic trioxide.

| Age (yrs) | No. of Relapses | Treatment duration (days) | Daily Dose (mg/kg) | Cumulative Dose (mg) | Time To Remission (days) | Platelets ≧100,000/ cu mm | Leukocytes ≧3,000/ cu mm |
|---|---|---|---|---|---|---|---|
| 36 | 1* | 36 | .16 | 360 | 54 | 36 | 54 |
| 45 | 3*[a] | 39 | .12 | 390 | 83 | 39 | 83 |
| 31 | 3[a,b] | 37 | .18 | 370 | 41 | 39 | 41 |
| 25 | 2 | 16 | .06 | 160 | 24 | 16 | 16 |
| 62 | 2*[d] | 30 | .11 | 300 | 41 | 41 | 31 |
| 75 | 1 | 12 | .20 | 180 | 30 | 30 | 30 |
| 40 | 1* | 33 | .16 | 495 | 47 | 47 | 43 |
| 13 | 2*[a,b] | 27 | .18 | 270 | 50 | 41 | 52 |
| 9 | 1* | 33 | .17 | 165 | 28 | 28 | 28 |
| 70 | 1[c] | 28 | .16 | 420 | 77 | 77 | 49 |
| 28 | 2* | 36 | .15 | 515 | 54 | 47 | 54 |
| 25 | 3 | 5 | .15 | 75 | † | † | † |

All patients had previously received one or more courses of all-trans retinoic acid, plus an anthracycline antibiotic plus cytosine arabinoside. * Denotes individuals with proven retinoid resistance (i.e. lack of response during reinduction or relapse while on retinoid maintenance); \ in patients with APL and in patients with other hematologic diseases. In patients with APL, marrow mononuclear cells were serially monitored by flow cytometry for immunophenotype, fluorescence in situ hybridization (FISH), and Western blot expression of the apoptosis-associated proteins, caspases 1, 2 and 3. Cells that coexpressed CD11b and CD33, and which by FISH analysis carried the t(15;17) translocation, progressively increased during treatment and persisted early in complete remission. $As_2O_3$ also induced in vivo expression of the proenzymes of caspase 2 and caspase 3, and activation of both caspase 1 and caspase 3. PK analysis of blood and urine for elemental arsenic (As) content showed that As was distributed in both plasma and red blood cell fractions of whole blood. Parallel elimination curves suggested that these 2 compartments were freely exchangeable, and decayed from peak values with initial half lives of about 60 mins. The mean AUC on day 1 was about 400 ng·hr/ml. Approximately 20% of the administered dose was recovered in urine within the first 24 hrs.

We then initiated a dose-ranging study in patients with diseases other than APL using a daily intravenous dosing schedule for a cumulative total of 25 days per treatment course every 3–5 weeks at dose levels of 0.1 and 0.15 mg per kg body weight per day. To date, 10 patients have been accrued, including patients with CLL (2 patients), AML (3 patients), lymphoma (4 patients), and CML (1 patient). Five patients were removed from the study early due to rapid progression, and 5 completed the planned 25-day course. Over this dose range, the drug has proved well-tolerated; adverse effects have included skin rash, lightheadedness during the infusion, fatigue, and QTc prolongation on EKG. Results from this ongoing study show that clinical use of $As_2O_3$ induces partial differentiation and apoptosis in APL, but that the therapeutic effects of this agent are not confined to this disorder.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Various publications are cited herein, the disclosures of which are incorporated by reference in their entireties.

What is claimed is:

1. A method for treating acute promyelocytic leukemia, comprising determining a dosage amount of arsenic trioxide for the treatment of a patient diagnosed with acute promyelocytic leukemia, based on the weight of the patient and a dose of 0.15 mg/kg of patient body weight, and administering arsenic trioxide in said dosage amount to said patient, wherein said arsenic trioxide is administered for a maximum of 60 days or until bone marrow remission, wherein said administering constitutes a first administration.

2. The method of claim 1, further comprising a second administration of 0.15 mg/kg arsenic trioxide for 25 doses.

3. The method of claim 2, wherein said second administration is administered 3 to 6 weeks after said first administration.

4. The method of claim 3, wherein said second administration is administered for up to five weeks.

5. The method of claim 4, wherein said second administration is administered at five doses per week.

6. The method of claim 2, further comprising repeating said second administration.

7. The method of claim 6, wherein said second administration is repeated every 3 to 6 weeks.

8. The method of claim 7, wherein said second administration is repeated until a total of between two and ten cycles of said second administration are completed.

9. The method of claim 8, further comprising repeating said second administration until a total of two cycles of said second administration are completed.

10. The method of claim 8, further comprising repeating said second administration until a total of ten cycles of said second administration are completed.

11. A method for treating acute promyelocytic leukemia in a human, comprising administering 0.15 mg/kg arsenic trioxide once per day, wherein said arsenic trioxide is administered for a maximum of 60 days or until bone marrow remission, wherein said administering constitutes a first administration.

12. The method of claim 11, further comprising a second administration of 0.15 mg/kg arsenic trioxide once per day for 25 doses.

13. The method of claim 12, wherein said second administration is administered 3 to 6 weeks after said first administration.

14. The method of claim 13, wherein said second administration is administered for up to five weeks.

15. The method of claim 14, wherein said second administration is administered at five doses per week.

16. The method of claim 12, further comprising repeating said second administration.

17. The method of claim 16, wherein said second administration is repeated every 3 to 6 weeks.

18. The method of claim 17, wherein said second administration is repeated until a total of between two and ten cycles of said second administration are completed.

19. The method of claim 18, further comprising repeating said second administration until a total of two cycles of said second administration are completed.

20. The method of claim 18, further comprising repeating said second administration until a total of ten cycles of said second administration are completed.

* * * * *

UNITED STATES PATENT AND TRADEMARK OFFICE
CERTIFICATE OF CORRECTION

PATENT NO. : 6,861,076 B2
DATED : March 1, 2005
INVENTOR(S) : Raymond P. Warrell, Jr., Pier Paolo Pandolfi and Janice L. Gabrilove It is certified that error appears in the above-identified patent and that said Letters Patent is hereby corrected as shown below:

Column 3,
Line 3, "chinese" should read -- Chinese --;
Line 17, "in vitro" should read -- *in vitro* --;
Line 50, "above" should read -- above, --;

Column 4,
Line 42, "Arsobale" should read -- Arsobale® --;

Column 5,
Line 63, "cell-s" should read -- cells --;

Column 6,
Line 62, "oesophagus" should read -- esophagus --;

Column 7,
Lines 10-11, "in vitro can readily be achieved in vivo." should read -- *in vitro* can readily be achieved *in vivo*. --;
Line 20, "is" should read -- are --;
Line 36, "(PLXF-RARa)" should read -- (PLXF-RARα) --;
Line 45, "are" should read -- is --;

Column 8,
Line 66, "sterilized" should read -- sterilized, --;

Column 9,
Line 56, "is" should be deleted;

Column 12,
Line 19, "formulation" should read -- formulations --;
Line 67, "in vitro" should read -- *in vitro* --;

Column 14,
Lines 3, 38 and 39, "in vitro" should read -- *in vitro* --;
Line 14, "in vivo" should be -- *in vivo* --;

Column 15,
Line 13, "This data indicates" should read -- These data indicate --;
Line 46-47, "in vitro" should read -- *in vitro*, --;
Line 50, "ex vivo" should read -- *ex vivo* --;
Line 54, "in vivo" should read -- *in vivo* --;
Line 65, "is" should read -- are --;

UNITED STATES PATENT AND TRADEMARK OFFICE
CERTIFICATE OF CORRECTION

PATENT NO. : 6,861,076 B2
DATED : March 1, 2005
INVENTOR(S) : Raymond P. Warrell, Jr., Pier Paolo Pandolfi, and Janice L. Gabrilove It is certified that error appears in the above-identified patent and that said Letters Patent is hereby corrected as shown below:

Column 16,
Line 67, "in situ" should read -- *in situ* --;

Column 17,
Line 13, "in situ" should read -- *in situ* --;
Line 20, "board" should read -- board. --;

Column 18,
Line 6, "in situ" should read -- *in situ* --;

Column 20,
Lines 13 and 16-17, "in situ" should read -- *in situ* --;
Line 29, "in vivo" should read -- *in vivo* --;

Column 21,
Line 4, "in situ" should read -- *in situ* --;
Line 28, "in vitro" should read -- *in vitro* --;
Line 29, "10-4" should read -- $10^{-4}$ --;
Line 67, "\" should read -- † --;

Column 22,
Line 10, "in vitro" should read -- *in vitro* --;
Line 32, "the" should be deleted;
Line 66, "in situ" should read -- *in situ* --;

Column 23,
Line 5, "in vivo" should read -- *in vivo* --;

UNITED STATES PATENT AND TRADEMARK OFFICE
CERTIFICATE OF CORRECTION

PATENT NO.    : 6,861,076 B2
DATED         : March 1, 2005
INVENTOR(S)   : Raymond P. Warrell, Jr., Pier Paolo Pandolfi, and Janice L. Gabrilove It is certified that error appears in the above-identified patent and that said Letters Patent is hereby corrected as shown below:

Column 24,
Lines 14, 17, 20, 43, 47 and 49, "are" should read -- is --.

Signed and Sealed this

Thirteenth Day of September, 2005

JON W. DUDAS
*Director of the United States Patent and Trademark Office*

UNITED STATES PATENT AND TRADEMARK OFFICE
CERTIFICATE OF CORRECTION

PATENT NO. : 6,861,076 B2
APPLICATION NO. : 10/758994
DATED : March 1, 2005
INVENTOR(S) : Raymond P. Warrell, Jr., Pier Paolo Pandolfi and Janice L. Gabrilove It is certified that error appears in the above-identified patent and that said Letters Patent is hereby corrected as shown below:

Column 3,
Line 3, "chinese" should read -- Chinese --;
Line 17, "in vitro" should read -- *in vitro* --;
Line 50, "above" should read -- above, --;

Column 4,
Line 42, "Arsobale" should read -- Arsobale® --;

Column 5,
Line 63, "cell-s" should read -- cells --;

Column 6,
Line 62, "oesophagus" should read -- esophagus --;

Column 7,
Lines 10-11, "in vitro can readily be achieved in vivo." should read -- *in vitro* can readily be achieved *in vivo*. --;
Line 20, "is" should read -- are --;
Line 36, "(PLXF-RARa)" should read -- (PLXF-RAR$\alpha$) --;
Line 45, "are" should read -- is --;

Column 8,
Line 66, "sterilized" should read -- sterilized, --;

Column 9,
Line 56, "is" should be deleted;

Column 12,
Line 19, "formulation" should read -- formulations --;
Line 67, "in vitro" should read -- *in vitro* --;

Column 14,
Lines 3, 38 and 39, "in vivo" should read -- *in vitro* --;
Line 14, "in vitro" should be -- *in vivo* --;

UNITED STATES PATENT AND TRADEMARK OFFICE
CERTIFICATE OF CORRECTION

PATENT NO.         : 6,861,076 B2
APPLICATION NO. : 10/758994
DATED                 : March 1, 2005
INVENTOR(S)       : Raymond P. Warrell, Jr., Pier Paolo Pandolfi and Janice L. Gabrilove It is certified that error appears in the above-identified patent and that said Letters Patent is hereby corrected as shown below:

Column 15,
Line 13, "This data indicates" should read -- These data indicate --;
Line 46-47, "in vitro" should read -- *in vitro,* --;
Line 50, "ex vivo" should read -- *ex vivo* --;
Line 54, "in vivo" should read -- *in vivo* --;
Line 65, "is" should read -- are --;

Column 16,
Line 67, "in situ" should read -- *in situ* --;

Column 17,
Line 13, "in situ" should read -- *in situ* --;
Line 20, "board" should read -- board. --;

Column 18,
Line 6, "in situ" should read -- *in situ* --;

Column 20,
Lines 13 and 16-17, "in situ" should read -- *in situ* --;
Line 29, "in vivo" should read -- *in vivo* --;

Column 21,
Line 4, "in situ" should read -- *in situ* --;
Line 28, "in vitro" should read -- *in vitro* --;
Line 29, "10-4" should read -- $10^{-4}$ --;
Line 67, "\" should read -- † --;

Column 22,
Line 10, "in vitro" should read -- *in vitro* --;
Line 32, "the" should be deleted;
Line 66, "in situ" should read -- *in situ* --;

Column 23,
Line 5, "in vivo" should read -- *in vivo* --;

UNITED STATES PATENT AND TRADEMARK OFFICE
CERTIFICATE OF CORRECTION

PATENT NO. : 6,861,076 B2
APPLICATION NO. : 10/758994
DATED : March 1, 2005
INVENTOR(S) : Raymond P. Warrell, Jr., Pier Paolo Pandolfi and Janice L. Gabrilove It is certified that error appears in the above-identified patent and that said Letters Patent is hereby corrected as shown below:

<u>Column 24,</u>
Lines 14, 17, 20, 43, 47 and 49, "are" should read -- is --.

This certificate supersedes Certificate of Correction issued September 13, 2005.

Signed and Sealed this

Tenth Day of October, 2006

JON W. DUDAS
*Director of the United States Patent and Trademark Office*

UNITED STATES PATENT AND TRADEMARK OFFICE
CERTIFICATE OF CORRECTION

PATENT NO. : 6,861,076 B2
APPLICATION NO. : 10/758994
DATED : March 1, 2005
INVENTOR(S) : Raymond P. Warrell, Jr., Pier Paolo Pandolfi and Janice L. Gabrilove It is certified that error appears in the above-identified patent and that said Letters Patent is hereby corrected as shown below:

Column 3,
Line 3, "chinese" should read -- Chinese --;
Line 17, "in vitro" should read -- *in vitro* --;
Line 50, "above" should read -- above, --;

Column 4,
Line 42, "Arsobale" should read -- Arsobale® --;

Column 5,
Line 63, "cell-s" should read -- cells --;

Column 6,
Line 62, "oesophagus" should read -- esophagus --;

Column 7,
Lines 10-11, "in vitro can readily be achieved in vivo." should read -- *in vitro* can readily be achieved *in vivo*. --;
Line 20, "is" should read -- are --;
Line 36, "(PLXF-RARa)" should read -- (PLXF-RAR$\alpha$) --;
Line 45, "are" should read -- is --;

Column 8,
Line 66, "sterilized" should read -- sterilized, --;

Column 9,
Line 56, "is" should be deleted;

Column 12,
Line 19, "formulation" should read -- formulations --;
Line 67, "in vitro" should read -- *in vitro* --;

Column 14,
Lines 3, 14 and 38, "in vitro" should read -- *in vitro* --;
Line 39, "in vivo" should be -- *in vivo* --;

UNITED STATES PATENT AND TRADEMARK OFFICE
CERTIFICATE OF CORRECTION

PATENT NO. : 6,861,076 B2
APPLICATION NO. : 10/758994
DATED : March 1, 2005
INVENTOR(S) : Raymond P. Warrell, Jr., Pier Paolo Pandolfi and Janice L. Gabrilove It is certified that error appears in the above-identified patent and that said Letters Patent is hereby corrected as shown below:

<u>Column 15,</u>
Line 13, "This data indicates" should read -- These data indicate --;
Line 46-47, "in vitro" should read -- *in vitro,* --;
Line 50, "ex vivo" should read -- *ex vivo* --;
Line 54, "in vivo" should read -- *in vivo* --;
Line 65, "is" should read -- are --;

<u>Column 16,</u>
Line 67, "in situ" should read -- *in situ* --;

<u>Column 17,</u>
Line 13, "in situ" should read -- *in situ* --;
Line 20, "board" should read -- board. --;

<u>Column 18,</u>
Line 6, "in situ" should read -- *in situ* --;

<u>Column 20,</u>
Lines 13 and 16-17, "in situ" should read -- *in situ* --;
Line 29, "in vivo" should read -- *in vivo* --;

<u>Column 21,</u>
Line 4, "in situ" should read -- *in situ* --;
Line 28, "in vitro" should read -- *in vitro* --;
Line 29, "10-4" should read -- $10^{-4}$ --;
Line 67, "\" should read -- † --;

<u>Column 22,</u>
Line 10, "in vitro" should read -- *in vitro* --;
Line 32, "the" should be deleted;
Line 66, "in situ" should read -- *in situ* --;

<u>Column 23,</u>
Line 5, "in vivo" should read -- *in vivo* --;

UNITED STATES PATENT AND TRADEMARK OFFICE
CERTIFICATE OF CORRECTION

PATENT NO. : 6,861,076 B2
APPLICATION NO. : 10/758994
DATED : March 1, 2005
INVENTOR(S) : Raymond P. Warrell, Jr., Pier Paolo Pandolfi and Janice L. Gabrilove It is certified that error appears in the above-identified patent and that said Letters Patent is hereby corrected as shown below:

Column 24,
Lines 14, 17, 20, 43, 47 and 49, "are" should read -- is --.

This certificate supersedes Certificate of Corrections issued September 13, 2005 and October 10, 2006.

Signed and Sealed this

Twenty-seventh Day of March, 2007

JON W. DUDAS
*Director of the United States Patent and Trademark Office*